(12) United States Patent
Keith (10) Patent No.: US 6,991,918 B2
(45) Date of Patent: Jan. 31, 2006

(54) METHODS FOR IMPROVING SENSITIVITY OF OXYGEN BIOSENSORS

(75) Inventor: Steven C. Keith, Chapel Hill, NC (US)

(73) Assignee: Becton Dickinson and Co.,, Franklin Lakes, NJ (US)

(*) Notice: Subject to any disclaimer, the term of this patent is extended or adjusted under 35 U.S.C. 154(b) by 460 days.

(21) Appl. No.: 09/966,505

(22) Filed: Sep. 28, 2001

(65) Prior Publication Data

US 2004/0106209 A1 Jun. 3, 2004

(51) Int. Cl.
*C12Q 1/22* (2006.01)

(52) U.S. Cl. .............................. 435/31; 435/34; 435/29

(58) Field of Classification Search ................. 435/31, 435/34, 29, 25, 817, 968; 436/172, 800
See application file for complete search history.

(56) References Cited

U.S. PATENT DOCUMENTS

| | | | | |
|---|---|---|---|---|
| 5,567,598 A | * | 10/1996 | Stitt et al. ...................... | 435/29 |
| 5,998,517 A | * | 12/1999 | Gentle et al. .................. | 524/92 |
| 6,080,574 A | * | 6/2000 | Berndt ..................... | 435/288.7 |
| 6,395,506 B1 | * | 5/2002 | Pitner et al. ................... | 435/32 |
| 6,538,735 B1 | * | 3/2003 | Duebendorfer et al. ..... | 356/318 |
| 6,616,896 B2 | * | 9/2003 | Labuda et al. ................. | 422/84 |
| 6,900,030 B2 | | 5/2005 | Stitt et al. | |

OTHER PUBLICATIONS

Bacon J. Determination of Oxygen Concentrations by Luminescence Quenching of a Polymer Immobilized Transition Metal Complex. Analytical Chemistry 69(23)2780-2785, 1987.*
Parker J. Chemical Sensors Based on Oxygen Detection by Optical Methods. SPIE 586, pp. 156-162, 1985.*
Wodnicka M. Novel Fluorescent Technology Platform for High Throughput Cytotoxicity and Proliferation Assays. J of Biomolecular Screening 5(3)141-152, Jun. 2000.*
U.S. Appl. No. 08/715,557, filed Sep. 18, 1996, Stitt et al.
U.S. Appl. No. 10/957,802, filed Oct. 4, 2004, Stitt et al.
U.S. Appl. No. 09/642,504, filed Aug. 18, 2004, Stitt et al.
U.S. Appl. No. 10/109,475, filed Mar. 28, 2002, Stitt el al.

* cited by examiner

*Primary Examiner*—Ralph Gitomer
(74) *Attorney, Agent, or Firm*—Scott J. Rittman (57) ABSTRACT

A method for detecting oxygen in a test sample is provided, the method involving exposing a test sample and a control sample to sensor compositions having a luminescent compound capable of generating a signal indicative of oxygen depletion. The method further involves determining the strengths of such signals for the test sample versus the control sample, and using the difference to determine whether oxygen in the test sample is being consumed.

14 Claims, 7 Drawing Sheets

Figure 2:
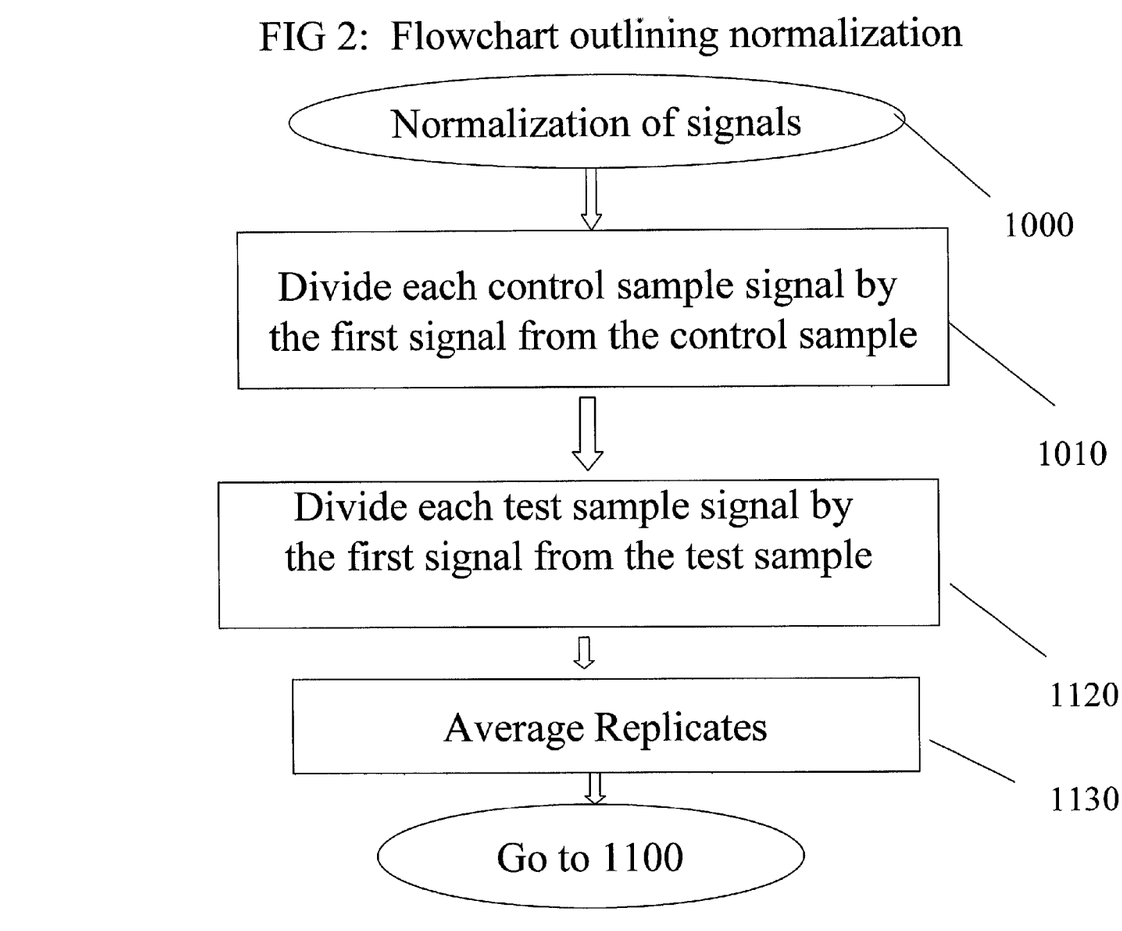

FIG 2: Flowchart outlining normalization

Figure 3:
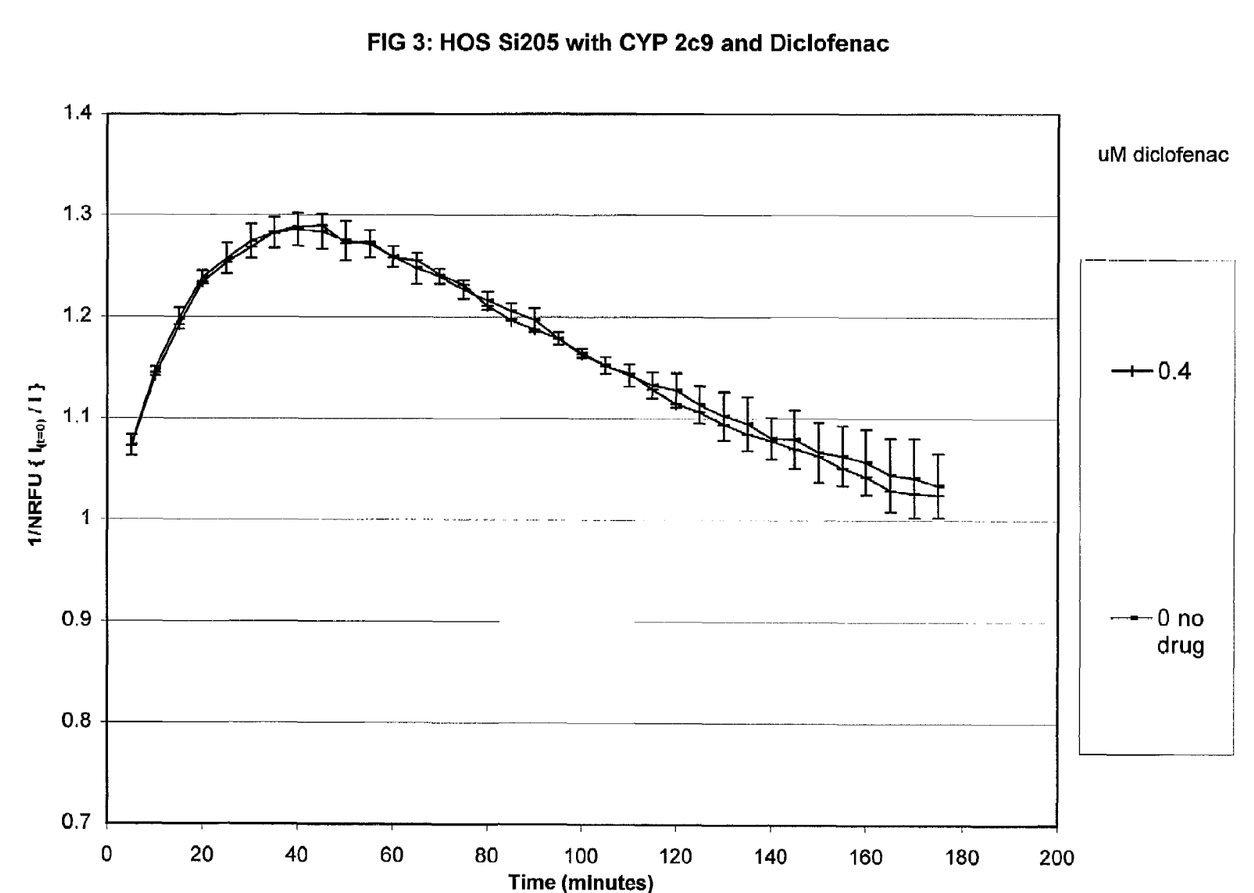

FIG 3: HOS Si205 with CYP 2c9 and Diclofenac

Figure 4:
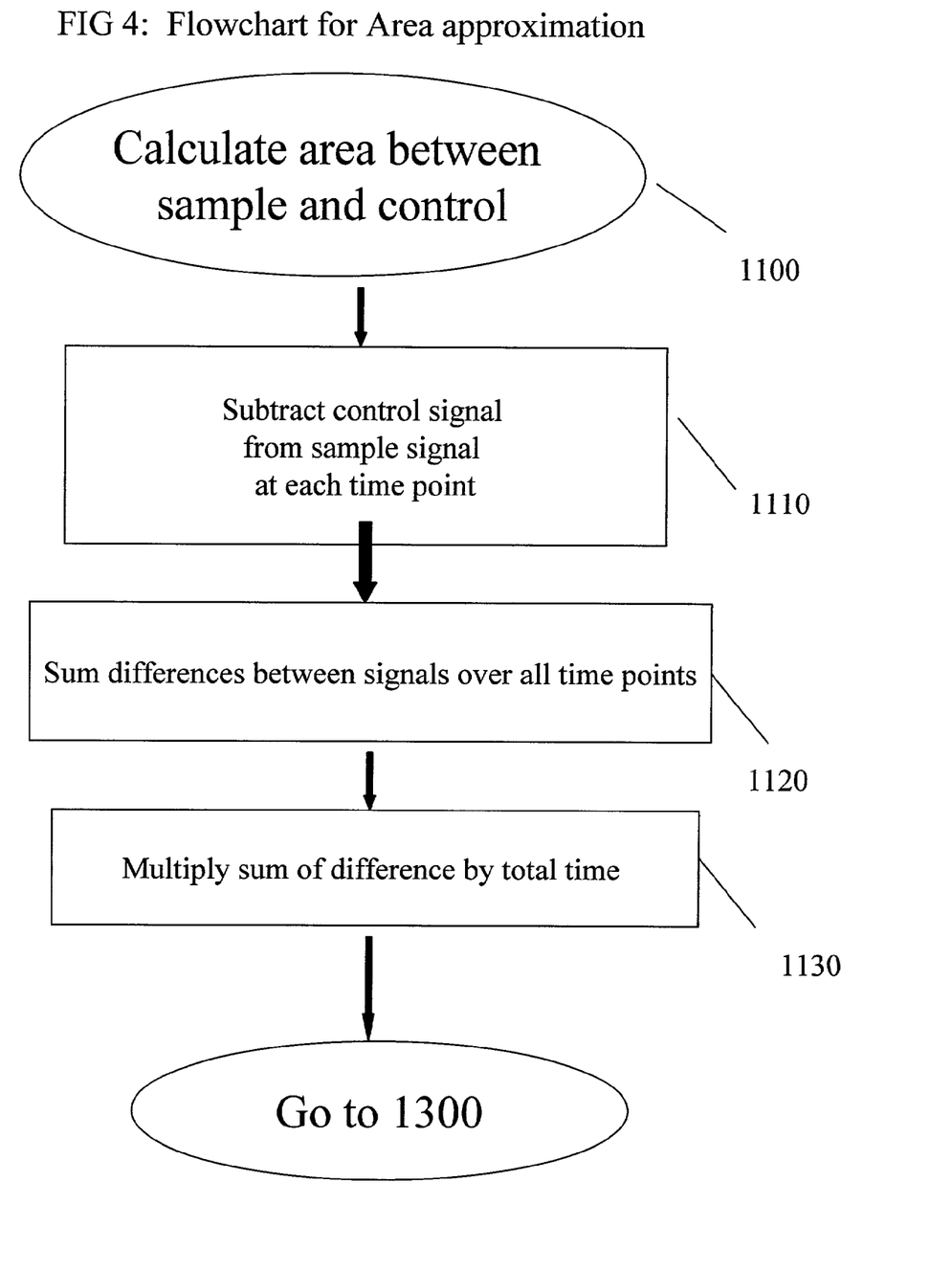

FIG 4: Flowchart for Area approximation

Figure 6:
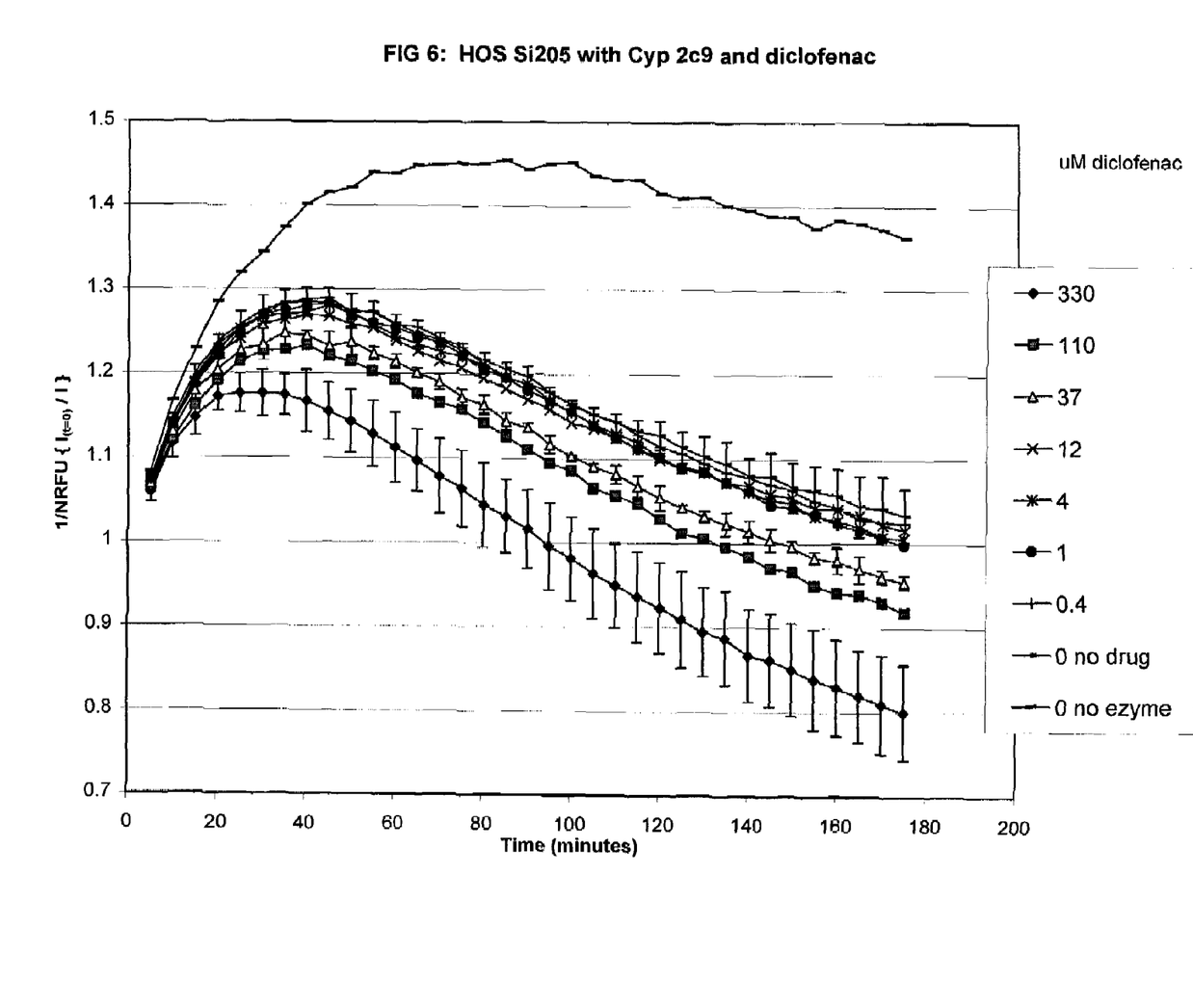

FIG 6: HOS Si205 with Cyp 2c9 and diclofenac

METHODS FOR IMPROVING SENSITIVITY OF OXYGEN BIOSENSORS

BACKGROUND OF THE INVENTION

1. Field of the Invention

The present invention relates to cell biology. In particular, this invention is directed to methods used to detect metabolic activity of biological samples based on their ability to consume oxygen.

2. Description of Relevant Art

Early knowledge about the metabolism of a new chemical entity (NCE) helps in the drug development process by providing important information for the selection of a lead compound from among a number of substances pharmacologically equally effective in their therapeutic response. In vitro metabolic studies may give information regarding the metabolic stability, toxicity, potential drug-drug interactions and the identification of the enzymes necessary for the metabolism of a compound.

The results of in vitro metabolic studies of an NCE determine to a great extent its future as a drug candidate. For example, if an NCE is rapidly metabolized, its bioavailability in vivo is most probably too low for it to be a drug. In vitro metabolic studies may reveal that an NCE can inhibit the binding of other drugs to enzymes, possibly resulting in prolonged pharmacological effects or an increased risk of drug toxicity. These results may be reason to eliminate it as a drug candidate.

NCEs and other chemical entities are mainly metabolized by enzymes in the liver, kidneys, gastrointestinal tract, skin, and lungs. Chemical entity-metabolizing enzymes are found in the endoplasmic reticulum of cells in these tissues and are classified as microsomal enzymes. There are 2 types of drug-metabolizing enzymes: phase I enzymes, or mixed function oxidases, which catalyze predominantly oxidation, reduction, and hydrolysis; and phase II enzymes, which catalyze glucuronidation, sulfation, or acetylation.

The majority of phase I metabolism is catalyzed by the cytochrome P-450 enzymes, which are heme-containing, membrane-bound proteins. These enzymes, found at highest concentration in the hepatocytes, biotransform lipophilic chemical entities to more polar compounds that can be excreted by the kidneys. The cytochrome P450's catalyze an oxidative reaction that is characterized by the oxidation of a substrate using atmospheric oxygen ($O_2$).

Several known in vitro assays utilize oxidation reactions to measure oxygen consumption in order to assess, for example, if a particular enzyme is capable of metabolizing a test compound. One known method involves exposing a chemical entity to one or more preparations of enzymes and then placing the samples in chemical communication with a luminescent compound such as ruthenium dye which is quenched in the presence of oxygen. As oxidation of the chemical entity occurs, oxygen in the sample will be consumed leading to an increase in fluorescence. The increase in fluorescence is taken as an indication of metabolization.

The fluorescent intensity data, ordinarily read by a fluorometer, may be analyzed by a variety of methods to ascertain whether a particular chemical entity is being metabolized. For instance, as further oxygen is consumed over time, the amount of fluorescence correspondingly increases. Accordingly, after a predetermined period of time has elapsed (e.g. 1 hour), the magnitude of fluorescence emission from a sample having the metabolized chemical entity may be much greater than the magnitude of fluorescence emission from a control, such as a sample not containing the chemical entity. The value of the last reading taken for the sample can be compared with the control. If the sample value is above the control value at the final time point, the sample is identified as a positive sample. However, if the last value taken of the sample is below the control value, the sample is identified as a negative sample.

Although this "endpoint" detection" method can generally be effective in identifying positive and negative samples, it's not uncommon for this method to incorrectly identify a positive sample as being negative. Discrimination between metabolizable or nonmetabolizable chemical entities involves detecting small differences between fluorescence signals. The sample value may not be significantly larger than the control value after replicate variances are taken into account at any particular time point even though the sample may be, in fact, positive.

Also, it may be desirable to use only a small amount of a chemical entity which may make it difficult to generate an oxygen consumption rate which is sufficiently higher than the control value even though the chemical entity may be effectively metabolized by particular enzymes. At any given time point, there may be no apparent variation between a control value and the sample, resulting in the conclusion that metabolism is not occurring.

Other methods have been developed as well. In one method, the overall change in magnitudes of a sample reading is calculated and compared to a known value having a magnitude indicative of a positive result. Accordingly, if the magnitude of change is greater than the predetermined value, the sample is identified as a positive sample. On the other hand, if the magnitude of change is less than the predetermined value, the sample is identified as a negative sample.

Although this method may be more effective than the endpoint detection method discussed above, certain flaws in this method also exist. For example, if a sample contains a highly metabolizable chemical entity, the amount of oxygen consumption may reach a maximum at the time the initial reading is taken, and increase very little throughout the duration of the reading period. In this event, the change which occurs between the initial readings and final readings is minimal even though the sample is positive. Hence, the sample may be incorrectly identified as a negative sample.

Accordingly, a continuing need exists for a method to analyze data representative of readings using luminescence based systems to accurately discriminate between small differences in luminesence signals.

SUMMARY OF THE INVENTION

In an aspect of the invention there is provided a method for detecting oxygen consumption in a test sample which includes:

(a) exposing a test sample to a sensor composition and a control sample to a sensor composition, said sensor composition including a luminescent compound being inhibited from generating a detectable signal in the presence of an inhibitory amount of oxygen and which generates a detectable signal as the inhibitory amount of oxygen is reduced;

(b) determining the strength of said signals generated by said sensor compositions exposed to test and control samples at time intervals;

(c) comparing the strengths of said signals generated from the sensor composition exposed to the test sample with the signals generated by the sensor composition exposed to said control sample over said time intervals and determining whether oxygen in the test sample has been consumed.

In another aspect of the invention there is provided an article of manufacture which includes computer useable medium and computer readable code embodied on said computer useable medium for detecting oxygen consumption in a test sample wherein the computer readable code is
(a) configured to receive of a plurality of signals generated at time intervals by a sensor composition exposed to a test sample and a sensor composition exposed to a control sample, wherein said sensor composition comprises an oxygen sensitive luminescent compound, said luminescent compound being inhibited from generating a detectable signal in the presence of an inhibitory amount of oxygen and which generates a detectable signal as the inhibitory amount of oxygen is reduced, said signals being provided by a user;
(b) computer readable program code devices configured to cause the computer to effect the comparing of the strengths of said signals generated from the sensor composition exposed to the test sample with the signals generated by the sensor composition exposed to said control sample over said time intervals and determining whether oxygen in the test sample has been consumed.

In another aspect of the invention there is provided a method in a computer system for detecting oxygen consumption in a test sample which includes:
(a) presenting a prompt to a user requesting a submission of signals generated at time intervals by a sensor composition exposed to a test sample and a sensor composition exposed to a control sample, said sensor composition comprising an oxygen sensitive luminescent compound, said luminescent compound being inhibited from generating a detectable signal in the presence of an inhibitory amount of oxygen and which generates a detectable signal as the inhibitory amount of oxygen is reduced;
(b) receiving said submission of signals;
(c) comparing the strengths of said signals generated from the sensor composition exposed to the test sample with the signals generated by the sensor composition exposed to said control sample over said time intervals and determining whether oxygen in the test sample has been consumed.
(d) indicating to the user if said signals indicate the consumption of oxygen in the test sample.

DETAILED DESCRIPTION

The present invention describes methods for detecting metabolic activity of test samples based upon their ability to consume dissolved oxygen. The methods utilize a fluorescence detection system which makes use of the sensitivity of the fluorescent emission of certain compounds to the presence of oxygen. Oxygen acts to quench (diminish) the compound's fluorescent emission in a concentration dependent manner. Metabolizing test samples will consume oxygen in a liquid medium, thereby affecting the oxygen concentration of the medium in which they are immersed. The present invention improves the sensitivity of the fluorescence detection system because it enables a researcher to determine whether or not a series of fluorescent signals observed over a period of time for a test sample are greater than for signals from a control sample observed over a period of time. For particular test samples, oxygen consumption may not be high overall and at any particular time point, a control sample may result in a similar signal to a test sample. The method of this invention enables similar fluorescent signals from control and test samples to be distinguishable so that over time, one can assess whether or not oxygen consumption occurring in a test sample is different from that occurring in a control sample.

In a preferred embodiment of the invention, oxidative reactions catalyzed by enzymes are detected based on their consumption of oxygen using the methods of the present invention. The enzymes are admixed with a chemical, drug or toxin to ascertain, for example, whether or not the enzymes are able to metabolize the chemical, drug or toxin.

Non-limiting examples of such enzymes include oxidative metabolic enzymes such as the CYP450 enzyme system, monamine oxidase (MAO) and flavin monooxygenase (FMO). In a preferred embodiment, the oxidative reactions are performed by metabolic enzymes in liver cells (hepatocytes) or cells which have been modified to express metabolic enzymes. The oxidative reactions can be performed by enzyme systems (several enzymes which together comprise a subcellular system) or enzymes as described above.

Non-limiting examples of enzymes in the CYP450 enzyme system include cytochrome P450 and P450 reductase which catalyze the majority of xenobiotics and many endogenous compounds. The CYP450's catalyze an oxidative reaction that is characterized by the oxidation of a substrate R using atomspheric oxygen ($O_2$). The reaction requires a reduced cofactor such as NADPH +H and can be expressed as the following reaction:

$NADPH+H+ +RH+O_2 \rightarrow NADP+ +ROH+H_2O$

It is contemplated, however, that the present invention may be used in other applications where it is desirable to detect oxygen consumption, including but not limited to, determining whether or not cell proliferation occurred in a test sample and determining the effect of a chemical, drug or toxin on cell proliferation or survival.

For example, the invention may be used to test the susceptibility of organisms or cells to a compound such as an antibiotic which is capable of severely inhibiting the growth of organisms or cells. The increase in luminescent signal normally caused by cells or organisms will be suppressed in the presence of such compounds. The behavior of the luminescent signal will demonstrate the ability of the chemical, drug or compound to negatively effect the normal oxygen consumption of the organisms or cells.

As used herein, a "test sample" may include but not be limited to cells, tissues, enzymes, subcellular systems, and microorganisms. Test samples as used herein, may include chemicals, drugs or toxins which may be admixed with the cells, tissues and the like. Cells, tissues, enzymes, subcellular systems, and microorganisms may be derived from eukaryotes or prokaryotes, plant or animal including fish, avian, and insect as well as fungal, algal, and bacterial cells or organisms, preferably mammals and even more preferably humans, rodentia, bovines and lagomorphs.

Examples of drugs and toxins which can be utilized in the process of the present invention include gallium nitrate, procarbazine, fludarabine, vinblastine, streptozotocin, pentostatin, mitoxantrone, hydroxyurea, piperazinedione, MGBG, 5-azacytidine, bisantrene, cytarabin, colchicine, cladribin, amsacrine, 6-thioguanine, aclaubicin, cisplatin, 5-fluorourocil, blemycin, mitomycin C, actinomycin D, methotrexate, mechlorethamine, melphalan, docetaxel, epirubicin, etoposide, vincristin, doxorubicin, teniposide, trimetrexate, topotecan, CPT 11, paclitaxel, gemcitabin, thymidine, acivicin, spirogermanium, cyclocytidine, zinostatin, flavone acctate, diglycoaldehyde, deazauridine, anguidine, PALA, aphidicolin, L-alanosine, maytansine, DQ-1, camptothecin, cremophor EL, homoharringtonine, sodium azide, DQ-2, and $HgCl_2$, but this is not intended to be limited to such drugs and toxins and can include any drug or toxin which can be utilized in the present invention.

Examples of chemicals, including components, compounds, amino acids, vitamins, salts, proteins, and others, which can be utilized in the process of the present invention include magnesium chloride, glucose, D-gallctose, L-valine, glutamine, phenylalanine, arginine, cystine, glutamine, histidine, isoleucine, leucine, lysine, methionine, threonine, trptophan, tyrosine, valine, biotin, choline, folate, nicotinamide, pantothenate, pyridoxal, thiamine, riboflavin, sodium chloride, potassium chloride, $NaH_2PO_4$, $NaHCO_3$, calcium chloride, insulin, transferrin, but this is not intended to be limited to such chemicals and can include any chemical which can be utilized in the present invention.

As used herein, a "control sample" is compared to a "test sample" in order to determine whether or not the cells, organisms, chemicals etc. contained in a test sample are exhibiting oxygen consumption different from a control sample. In one aspect of the invention, the control sample is one which does not contain the compound or chemical for which cell metabolism and subsequent consumption of oxygen is to be determined. For example, such a control sample may contain cells, tissues, enzymes, chemicals, toxins, or drugs. In a preferred embodiment of the present invention, a test sample containing enzymes and a chemical of interest is compared to a control sample which only contains enzymes, the purpose being to assess the effect of the enzymes' ability to metabolize the chemical. The materials and/or cells contained in a control sample will depend, therefore, on the hypothesis or test purpose being tested.

In one aspect of the invention, a test sample and a control sample are each independently contacted with a sensor composition. A "sensor composition" includes a luminescent compound. The term luminescence is intended to include fluorescence and phosphorescence, as well as time-resolved fluorescence and fluorescence lifetime. In a preferred embodiment, the luminescent sensor compound can be a fluorescent sensor compound. In the process of the present invention, this compound is irradiated with light containing wavelengths which cause it to fluoresce, and the fluorescence is measured by any standard means.

The fluorescent compound must be one which exhibits a large quenching upon exposure to oxygen at a concentration ordinarily found in test cells in solution (generally 0.4%). As used herein an "inhibitory amount of oxygen" is one which precludes a detectable signal from the fluorescent compound. While virtually any such compound can be used, preferred fluorescent compounds of this invention are tris-2,2-bipyridyl ruthenium (II) salts, especially the chloride hexahydrate salt $(Ru(BiPy)_3Cl_2)$, tris-4,7-diphenyl-1,10-phenanthroline ruthenium (II) salts, especially the chloride salt $(Ru(DPP)_3Cl_2)$, and 9,10-diphenyl anthracene (DPA).

It is also considered that the luminescent sensor compound which is an oxygen sensor, can be a phosphorescent compound such as platinum (II) and palladium (II) octaethyl porphyrin complexes immobilized in PMMA (polymethyl methacrylate); CAB (cellulose acetate brityrate); platinum (II) and palladium (II) octaethyl porphyrin ketone complexes immobilized in PVC (polyvinylchloride) and polystyrene.

In a preferred embodiment of this invention, the fluorescent compound is chosen such that it will exhibit little or no fluorescence in the presence of oxygen.

In another aspect of the invention, the luminescent compound can be mixed and distributed throughout a plastic or rubber phase that is permeable to oxygen gas, but relatively impermeable to water and non-gaseous solutes. Silicone rubber is a particularly useful material for this application. When a test sample containing, for example enzymes and drug, is placed in a sample reservoir on the silicone rubber, the metabolic activity of the cells causes a reduction in the level of dissolved oxygen in the sample, and the sample will yield a higher luminescent signal upon excitation. Controls not containing drug or enzyme will not show as much of a decrease in their oxygen levels and will only show low levels of luminescence due to high oxygen quenching of the luminescent compound.

The fluorescent compound must be placed in chemical communication with the oxygen of the test sample to exhibit quenching. This can be achieved by placing the compound directly in contact with the sample. However, in a preferred embodiment the compound and sample are separated from each other by the interposition there between of a membrane embedding material permeable to oxygen and relatively impermeable to the other sample components thereby preventing the interaction of the sample and the compound. Neither the fluorescent compound nor the membrane in which the fluorescent compound is embedded need be in direct contact with the test sample, broth or fluid.

In one aspect of the invention, it has also been found that for systems where the compound or compound embedded membrane is in contact with a test or control sample, accurate results can be obtained when the system is left exposed to atmospheric oxygen. Thus, the system of this invention is quite versatile, and can be used in a wide array of conditions.

In one desirable embodiment, the fluorescent compound and test and control sample are substantially isolated from atmospheric oxygen, thereby preventing any false reading due to the presence of atmospheric oxygen, but still permitting reaction of the compound to the presence or absence of oxygen as a result of the diffusion of oxygen through a membrane. For example, isolation of the samples from atmospheric oxygen can be accomplished by an inert layer of fluid such as mineral oil placed over the control and test samples.

Alternatively, the oxygen sensitive fluorophore or luminesence compound can be in a microencapsulated form or in the form of granules of an oxygen permeable material. It is also anticipated that the fluorophore or luminescent compound can be contained within a separately manufactured component such as a bead, disc or prongs, which can be separately introduced into the test sample. The use of prongs is particularly advantageous as such prongs can be attached to a lid or other device to permit easy manipulation. In a desired embodiment, a plurality of prongs can be attached to a single membrane, or other cover and thereby be maintained in an appropriate orientation such that they can simultaneously be placed into the reservoirs of a base containing a plurality of sample reservoirs. By choice of appropriate materials, the prongs can be made impermeable to the microorganisms, cells and the like in the sample, but permeable to oxygen.

Use of the method can be facilitated by construction of a unitized apparatus. The apparatus may include a sample-containing reservoir, or more commonly a plurality of identical reservoirs adapted to contain a test sample and other such liquid and soluble components (e.g. nutrients, etc) as may be required by the particular application. The reservoirs also provide a luminescent sensor composition which monitors the oxygen levels of the solution. The sensor composition of this invention uses a luminescent compound known to show a large quenching of its luminescent emission when exposed to oxygen.

In a particularly desirable aspect of the invention, oxygen sensors are incorporated into a microwell tray format for detection of drug metabolism by enzyme preparations. The microwell format enables reading with routine luminescence plate readers. This format offers ease of use in a non-destructive assay in which no additional reagents are required. This feature allows oxidative reactions catalyzed by enzymes to be repeatedly monitored since no dyes or indicators are added to or released into the cellular media. The oxidative reactions monitored in the wells may thus be removed and used for additional assays if desired. Because this method is readily adapted to microwell tray formats such as 96 well and 384 well plates, the method is especially useful for high throughput screening of drugs, toxins and other chemicals to determine their oxygen consumption by enzymes.

The system may be read as frequently as the user's reading device will allow, to facilitate the generation of kinetic data. The reading device used to detect fluorescent intensity can be performed by any means ordinarily used for such measurements, e.g. a fluorometer. The fluorescent intensity is compared with a control sample (e.g. a system containing no enzymes or a system with no added test chemicals).

In a preferred embodiment, the oxygen sensor plates are prepared using 96 well microtiter plates following general methods described herein. In general, a sample reading is taken at a particular interval in time, and additional readings are taken at respective intervals in time for a predetermined duration of time.

For illustrative purposes, the operations for carrying out a preferred embodiment of the methods of the invention are described below with regard to a single test sample and a single control sample. This illustration is not meant to limit the invention in any way.

In the present illustration, a sample reading is obtained at approximately five-minute intervals for a period of 175 minutes. There are three replicates taken at each time interval including three replicates taken at the beginning of the period. Accordingly, 108 readings of each test sample and 108 readings of each control sample, are obtained during the 175 minute period.

A reading is a measurement of the intensity of the fluorescent emission being generated by a sample in response to excitation light emitted toward the test sample. These intensity values are stored in magnitudes of relative fluorescent units (RFUs). As used herein a "signal" is equivalent to an RFU. A reading of a sample having a high magnitude or strength of fluorescent emission will provide an RFU value higher than that provided by a reading taken of a sample having low fluorescent emission indicating a higher amount of oxygen consumption.

Readings can be obtained with a fluorimeter such as that which can be purchased from BMG Lab Technologies (Durham, N.C.). Because intensity readouts on fluorescence plates are in arbitrary units, values are "normalized" as used herein by dividing well values at selected time points by the same well's initial reading. Normalized RFU readings are referred to as "NRFU".

In one embodiment, a user will transmit an input file containing the data comprised of signals from control samples and test samples into a computer containing software which will perform various operations on the data representing the sample well readings.

Once the total number of readings for each sample and control have been taken, the readings may be interpreted by a computer which can indicate whether the test sample has tested positive or negative for oxygen consumption. The computer is controlled by software to perform various operations on the data representing the sample and control readings. The operations described below are applied in essentially the same manner to the readings taken for each sample and control.

For illustrative purposes, test sample readings from 0.4 micromolors of the drug, diclofenac, admixed with microsomes expressing P450 enzymes are read by a Polarstar fluorometer. (See below for details of reaction conditions). These signals are initially represented as $s_{raw1}$ through $s_{raw108}$. After normalization, the sample readings are represented as $Ns_{raw1}$ through $Ns_{raw108}$. After normalization, the replicates are averaged, their standard deviations and variances are determined and the test sample signals are represented as $Ns_1$ through $Ns_{35}$.

Additionally, during each five-minute interval, an optical detector from a fluorometer such as that seen in the Polarstar fluorometer obtains a "control" reading. Accordingly, after 108 readings, control reading are represented as $c_{raw1}$ through $c_{raw108}$. After normalization, the control readings are represented as $Nc_{raw1}$ through $Nc_{raw108}$. After normalization, the replicates are averaged, their standard deviations and variances are determined and the control sample signals are represented as $Nc_1$ through $Nc_{35}$.

Figure 1:
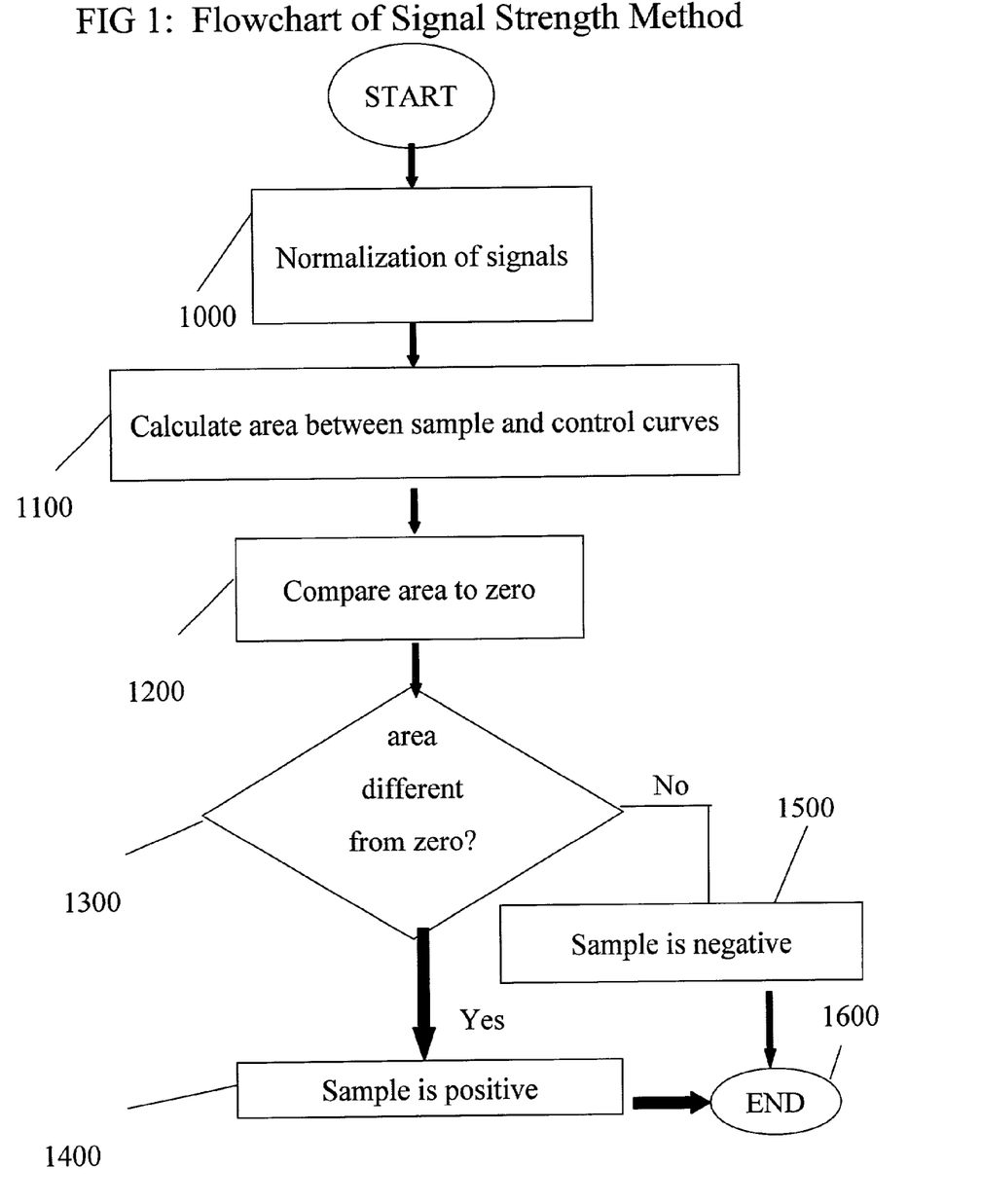

The flowchart shown in FIG. 1 represents the overall process for interpreting the raw data readings, $s_{raw1}$ through $s_{raw108}$ and $c_{raw1}$ through $c_{raw108}$, to provide a result which is used to determine whether the test sample includes greater oxygen consumption in comparison to the control sample. These processes are performed by software, which can be stored in a memory resident in a computer or on a disk inserted into a disk drive or other computer readable medium with a computer readable code embodied on the medium.

As shown in FIG. 1, the software initially controls the computer to perform a normalization on the data readings $s_{raw1}$ through $s_{raw108}$ and $c_{raw1}$ through $c_{raw108}$ (step 1000). In particular, in step 1010 of FIG. 2, the reading from each sample well is divided by the first sample reading $S_{raw1}$ to provide corrected normalized readings $Ns_{raw1}$ through $NS_{raw108}$. Likewise, the reading from each control well (step 1020) is divided by the first sample reading $Ns_{raw1}$ to provide corrected normalized readings $Nc_{raw1}$ through $Nc_{raw108}$. In this embodiment, the reciprocal of the normalized readings is used, i.e readings $1/Ns_{raw1}$, through $1/Ns_{raw108}$ and readings $1/Nc_{raw1}$ through $1/Nc_{raw108}$. As previously described, this example included three readings taken at each time point for both the samples and the controls. These replicates are averaged (step 1030), resulting in 35 readings each for the sample and control representing time points taken every five minutes from five minutes to 175 minutes, (i.e 35 readings) now represented as $1/Ns_1$ through $1/Ns_{35}$ and $1/Nc_1$ through $1/Nc_{35}$.

In one embodiment, step 1030 may additionally contain the determining of standard deviations of the averages and the variances.

FIG. 3 is a graph showing an exemplary relationship of the 70 readings for the sample and control after normalization and averaging (i.e $Nc_1$ through $Nc_{35}$) which have been obtained during the 175 minute reading period. These readings are plotted on the graph of FIG. 3 with their averaged NRFU values being represented as a reciprocal on the vertical axis with respect to time in minutes at which the readings were taken during the reading period (i.e $1/Nc_1$ through $1/Nc_{35}$ are plotted in FIG. 3).

As may be appreciated from the graph, the NRFU values for the readings taken later in the reading period are typically greater than the NRFU values of the readings taken at the beginning of the reading. The reciprocal is used here because NRFU is inversely related to $O_2$. Therefore, more oxygen is consumed as the reactions progress. As may also be appreciated from the graph, it is difficult to determine whether or not the control sample, which does not contain the drug, but does contain enzymes, exhibits a different amount of oxygen consumption in comparison to the test sample. As is evident from the error bars, the difference between a sample's signal and a control signal, at any instant in time, may be less than the errors associated with those signal measurements. The process that will now be described shows how a preferred analysis will reveal differences between these test and control signals.

The processing then proceeds to step 1100 in FIG. 4 in which the area between the sample and control curves are calculated. In this embodiment, since reciprocals are used, the averaged normalized control at each time point are added to the negative averaged normalized sample at each time point (step 1110). That is, the averaged normalized control reading $1/Nc_1$ is added to the negative averaged normalized sample reading $-(1/Ns_1)$ to provide corrected normalized sample reading $1/cNs_1$. Averaged normalized control reading $1/Nc_2$ is added to negative averaged normalized sample reading $-(1/Ns_2)$ to provide corrected normalized reading $1/cNs_2$ and so on. Additionally, the averaged normalized control reading $1/Nc_1$ is added to the negative averaged normalized control reading $1/Nc_1$ to provide corrected normalized control reading $1/cNc_1$; and averaged normalized control reading $1/Nc_2$ is added to negative averaged normalized control reading $1/Nc_2$ to provide corrected normalized reading $1/cNc_2$ and so on.

After all of the corrected normalized readings are obtained, the processing then continues to step 1120 where the corrected normalized readings are summed together at each time point. At five minutes, the integrated signal is equal to $1/cNc_1$. At ten minutes, the integrated signal is equal to $1/cNc_1 + 1/cNc_2$. At fifteen minutes, the integrated signal is equal to $1/cNc_1 + 1/cNc_2 + 1/cNc_3$ and so on. At step 1130 these differences are multiplied by the total time. In this illustration, the integrated signal calculated at the $35^{th}$ time point is multiplied by 175 to approximate the area between test sample and control curves.

The "area between the sample and control curve" as used herein, is defined by the following equation which uses the reciprocal values of the averaged normalized readings:

$$Area = \sum_{(i=1 \text{ to } n)} \{(1/Ns_i - 1/Nc_i) \times \Delta t\}$$
$$= \sum (i = 1 \text{ to } n)\{(1/Ns_i - 1/Nc_i)\} \times T$$
$$= \Delta t,$$

over a total time "T", where data is sampled n times at a particular time interval (e.g. 1 minute to several hours).

In an alternative embodiment, the control sample is influenced only by temperature. In this case, the signals from the control sample can be re-normalized to a constant value of 1 and test sample signals are renormalized through division so that $Ns_i^* = Ns_i/Nc_i$, so that $1/Ns_i^* = Nc_i/Ns_i$.

In this case, the Area calculation is simplified:

$$Area = \sum_{(i=1 \text{ to } n)} \{(1/Ns_i/1/Nc_i - 1/Nc_i/1/Nc_i) \times \Delta t\}$$
$$= \sum_{(i=1 \text{ to } n)} \{(1/Ns_i^* - 1)\} \times T$$
$$= \sum_{(i=1 \text{ to } n)} \{(1/Ns_i^*)\} - n) \times T.$$

The processing beginning at step 1300 for determining whether the test sample resulted in oxygen consumption different from the oxygen consumption from the control sample is shown in the flowchart of FIG. 1. In particular, in step 1300 the area between the test sample and control sample curves, which has been obtained by the above processing, is compared to 0. If the area is greater than 0, the processing proceeds to step 1400 where software controlling the computer provides an indication that the test sample has tested, as in this example, positive for metabolization of diclofenac. This indication can be in the form of a display on a display screen, in the form of data stored to a disk in a disk drive and/or in the form of data printed out by a printer.

However, if the processing determines, in step 1300, that the magnitude of the area is less than 0, the processing proceeds to step 1500 where software controlling the computer provides an indication that the test sample has tested negative, as in this example, for metabolization of diclofenac, or in other words, does not include detectable oxygen consumption greater than that of the control sample.

Figure 5:
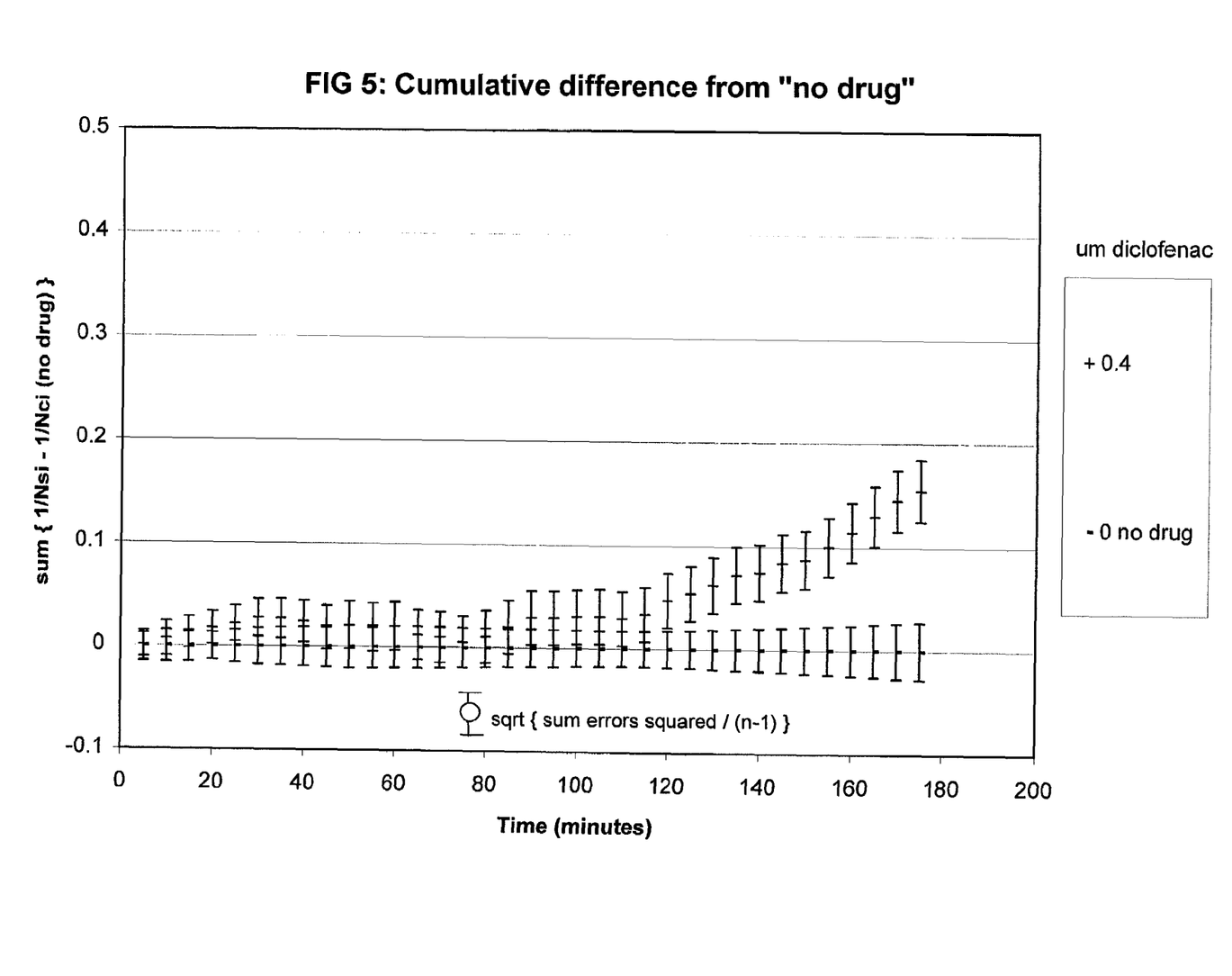

FIG. 5 is a graph showing the relationship of the 70 readings for the test sample and control sample after step 1120. These readings which represent $1/cNs_1$ through $1/cNs_{35}$ and $1/cNc_1$ through $1/cNc_{35}$ at each time point are plotted on the graph of FIG. 5. As may be appreciated from the graph there is greater oxygen consumption in the test sample than in comparison to the control sample. The signals from the test samples after 120 minutes differ from those from the control signal by amounts larger than the error.

EXAMPLES

The following examples illustrate certain preferred embodiments of the instant invention, but are not intended to be illustrative of all embodiments.

Example 1

This example illustrates how the microsomes containing P450 enzymes and the drug, diclofenac were prepared.

The cytochromes ("CYP") P450 are a large family of proteins found predominantly in the liver, involved in the metabolism or detoxification of substances in the body such as chemicals, hormones or natural food substances. While there are many different sub-families of CYP450, the isozyme families primarily involved in the metabolism of xenobiotics are the CYPs 3A, 2C, 2D and 1A.

Microsomes prepared from human lymphoblasts transfected with human CYP-2C9 were purchased from Gentest. Reaction buffer was prepared according to Gentest (100 mM Tris) to which was added 3.3 mM MgCl2 and a regenerating system: 1 mM NADP+, 3.3 mM Glucose-6-phosphate and 0.4 units/ml glucose-6-phosphate dehydrogenase (Sigma, St. Louis, Mo.). Reaction buffer (195 microliters/well) was plated onto a 96 well BD oxygen sensor plate (Becton Dickinson, Beford, Mass.) and equilibrated to 37° for 30 minutes.

Diclofenac, a known substrate of CYP-2C9, was added to the reaction mixture of certain wells prior to plating such that its final concentration was either 330 $\mu$M, 110 $\mu$M, 37 $\mu$M, 12 $\mu$M, 4 $\mu$M, 1 $\mu$M or 0.4 $\mu$M. In certain wells (control samples) no drug was added. Reaction was initiated by the addition of 10 P mol/well CYP-2C9. In certain wells, neither drug nor CYP-2C9 was added. 50 $\mu$l of mineral oil was added on top of the aqueous media to minimize the rate of oxygen diffusion into the media from the atmosphere.

Example 2

This example depicts the results from the BD oxygen biosensor plate (BD Biosciences, Bedford, Mass.) when diclofenac was added at different concentrations to microsomes expressing CYP450 enzymes.

All samples prepared as described in Example 1 were monitored for oxygen consumption using a BD oxygen biosensor plate. All data were obtained with a BMG Polarstar fluorimeter at 37° C. using the bottom plate reading configuration. The bandpass filters were 465 nm for excitation and 590 nm for emission. Data were obtained at the start of the experiment and then every five minutes for each concentration of drug, the control sample which did not contain drug and the sample which contained neither microsomes or drug. Three replicates for each condition at each reading were taken. Data were read at time intervals for a total time of 175 minutes. Data were normalized by dividing the first reading for each well by the subsequent readings. The reciprocal of these reading were used for subsequent calculations.

FIG. 6 shows a graph of these data. The X axis shows the time in minutes and the Y axis shows the reciprocals of the normalized relative fluorescent time units at each time point. As can be seen from the graph, when the data is presented without further processing, the difference between test sample signals and control sample signals (signals from microsomes not containing any diclofenic) needs to be larger than the replicate variances after a period of time and the differences need to remain large enough to discern from the graph. As can be seen from the FIG. 6, only test samples containing greater than 37 $\mu$M fulfill that criteria after 20 minutes. Signals from 0.4 $\mu$M to 12 $\mu$M diclofenac do not fulfill that criteria even after 175 minutes.

Example 3

This example depicts the cumulative difference from the control sample which does not contain any diclofenic for each test sample containing different concentrations of diclofenic.

Figure 7:
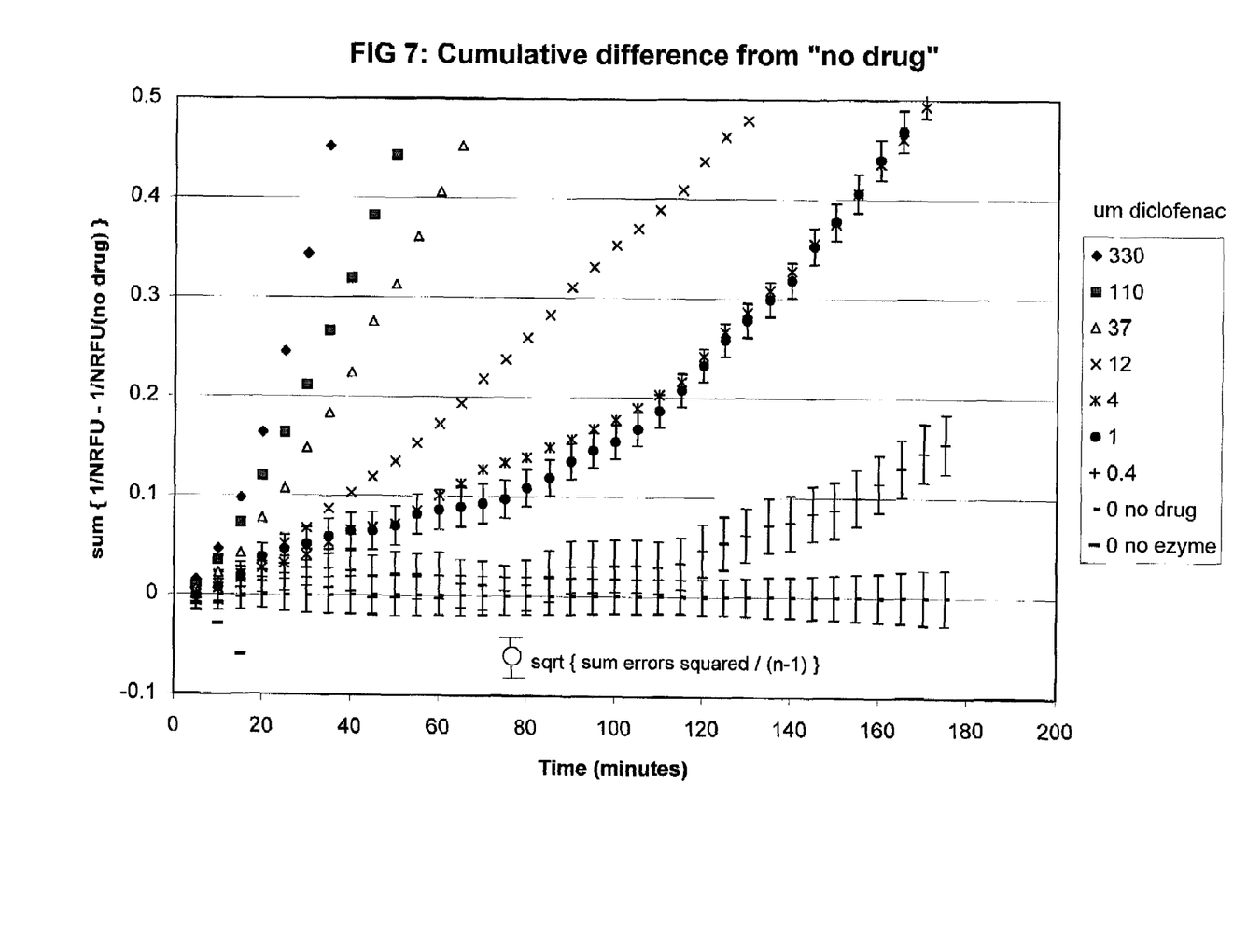

Each sample and control reading was analyzed as described above for test and control samples. The sum of the differences between sample and control signals from each time interval are plotted in FIG. 7. As is evident from FIG. 7, the method of the invention improves the ability to differentiate between test sample and control sample signals by accumulating the differences between the test and control sample signals while decreasing the error associated with those accumulated signals. Referring to FIG. 7, the integrated signals from 0.04 $\mu$M through 12 $\mu$M diclofenic differ from the integrated control signal by amounts larger than the error, even though individual measurements did not. The error is calculated as the cumulative residual sum of squares error (RSS) from the control sample: Sqrt{sum error/(n−1)}. Sensitivity to drug metabolism in this case was improved 90-fold. If the test were constrained to 40 minutes, the sensitivity would still have been increased by nearly 40-fold.

Various other changes and modifications may be effected therein by one skilled in the art without departing from the scope or spirit of the invention, and it is intended to claim all such changes and modifications as fall within the scope of the invention.

I claim:

1. A method for detecting oxygen consumption in a test sample comprising:
    exposing a test sample to a first sensor composition and a control sample to a second sensor composition, said first and second sensor composition comprising a luminescent compound being inhibited from generating a detectable signal in the presence of an inhibitory amount of oxygen and which generates a detectable signal as the inhibitory amount of oxygen is reduced;
    determining the strength of a first said detachable signals generated by said first sensor composition at time intervals;
    determining the strength of a second said detectable signal generated by said second sensor composition at said time intervals;
    comparing the strengths of said first signal with said second signal over said time intervals and determining whether oxygen in said test sample has been consumed wherein said comparing step comprises:
        normalizing said first said detectable signals and said second said detectable signals, said normalizing step comprising:
            dividing each said first said detectable signal by an initial said first said detectable signal; and
            dividing each said second said detectable signal by an initial said second said detectable signal;
        calculating the area between curves representative of said normalized first said detectable signals and said normalized said second said detectable signals; and
        comparing said area to zero.

2. The method according to claim 1, wherein said calculating step comprises the step of subtracting said second said detectable signal from said first said detectable signal at each said time interval to provide a corrected first said detectable signal for each said time interval.

3. The method of claim 1, wherein said luminescent compound is contained within a matrix which is relatively impermeable to water and non-gaseous solutes, but which is permeable to oxygen.

4. The method of claim 3, wherein said matrix is a rubber or plastic matrix.

5. The method of claim 3, wherein said matrix is a silicone rubber matrix.

6. The method of claim 1, wherein said luminescent compound is a tris-4,7-diphenyl-1,10-phenanthroline ruthenium (II) salt.

7. The method of claim 6, wherein said luminescent compound is tris-4,7-diphenyl-1,10-phenanthroline ruthenium (II) chloride.

8. The method of claim 1, wherein said luminescent compound is a tris-2,2'-bipyridyl ruthenium (II) salt.

9. The method of claim 8, wherein said luminescent compound is tris-2,2'-bipyridyl ruthenium (II) chloride hexahydrate.

10. The method of claim 1, wherein said luminescent compound is 9,10-diphenyl anthracene.

11. A method according to claim 1, wherein said test sample and said control sample are substantially isolated from atmospheric oxygen.

12. A method according to claim 1, wherein said test sample comprises a reaction mixture of at least one enzyme which catalyzes oxidative reactions, admixed with a quantity of at least one drug, toxin or chemical.

13. The method of claim 12, wherein said at least one enzyme comprises enzymes in liver cells.

14. The method of claim 12, wherein the at least one enzyme comprises a cytochrome P450 enzyme.

* * * * *